United States Patent
Munakata et al.

(10) Patent No.: US 10,450,934 B2
(45) Date of Patent: Oct. 22, 2019

(54) CATALYST DETERIORATION DETECTING SYSTEM AND CATALYST DETERIORATION DETECTING METHOD

(71) Applicant: MITSUI MINING & SMELTING CO., LTD., Tokyo (JP)

(72) Inventors: Naoki Munakata, Saitama (JP); Katsumasa Horii, Saitama (JP); Yunosuke Nakahara, Saitama (JP)

(73) Assignee: MITSUI MINING & SMELTING CO., LTD., Tokyo (JP)

( * ) Notice: Subject to any disclaimer, the term of this patent is extended or adjusted under 35 U.S.C. 154(b) by 0 days.

(21) Appl. No.: 16/077,528

(22) PCT Filed: Jul. 26, 2017

(86) PCT No.: PCT/JP2017/027121
§ 371 (c)(1),
(2) Date: Aug. 13, 2018

(87) PCT Pub. No.: WO2018/025729
PCT Pub. Date: Feb. 8, 2018

(65) Prior Publication Data
US 2019/0055872 A1 Feb. 21, 2019

(30) Foreign Application Priority Data
Aug. 4, 2016 (JP) .................. 2016-154064

(51) Int. Cl.
*G01K 13/02* (2006.01)
*F01N 11/00* (2006.01)
(Continued)

(52) U.S. Cl.
CPC ............ *F01N 11/002* (2013.01); *B01D 53/94* (2013.01); *F01N 3/00* (2013.01); *F01N 3/101* (2013.01);
(Continued)

(58) Field of Classification Search
CPC .... F01N 11/00; F01N 2560/06; F01N 11/002; F01N 2900/14; F01N 2550/02;
(Continued)

(56) References Cited

U.S. PATENT DOCUMENTS 5,388,454 A * 2/1995 Kuroda .................. F02D 41/22
73/114.75
5,526,643 A * 6/1996 Mukaihira .............. F01N 9/005
60/276
(Continued)

FOREIGN PATENT DOCUMENTS

CN         1796755 A     7/2006
CN      101512130 A     8/2009
(Continued)

OTHER PUBLICATIONS

International Search Report dated Sep. 12, 2017 filed in PCT/JP2017/027121.

*Primary Examiner* — Gail Kaplan Verbitsky
(74) *Attorney, Agent, or Firm* — Rankin, Hill & Clark LLP

(57) ABSTRACT

A system (9) of the invention is a system for detecting deterioration of a catalyst (8) provided in an exhaust passage (12) of an internal combustion engine (11), the system including: means (5) that detects a temperature of an exhaust on an upstream side of the catalyst (8); means (6) that detects a temperature of the exhaust on a downstream side of the catalyst (8); a recognition unit (10) that recognizes, both upstream and downstream of the catalyst (8), a change point at which the temperature changes from temperature fall or constant temperature to temperature rise during acceleration operation, or a change point at which the temperature changes from temperature rise or constant temperature to temperature fall during deceleration operation; and a determination unit (10) that determines that the catalyst (8) has
(Continued)

deteriorated when a difference (ΔT or ΔT') between the upstream and downstream change points becomes equal to or longer than a predetermined time.

7 Claims, 6 Drawing Sheets

(51) Int. Cl.

| | | |
|---|---|---|
| *B01D 53/94* | (2006.01) | |
| *F01N 3/20* | (2006.01) | |
| *F02D 45/00* | (2006.01) | |
| *F01N 3/00* | (2006.01) | |
| *G01K 1/14* | (2006.01) | |
| *G01K 7/02* | (2006.01) | |
| *F01N 3/10* | (2006.01) | |
| *G01K 7/06* | (2006.01) | |
| *G01N 25/72* | (2006.01) | |

(52) U.S. Cl.
CPC .............. *F01N 3/103* (2013.01); *F01N 3/20* (2013.01); *F02D 45/00* (2013.01); *G01K 1/14* (2013.01); *G01K 7/02* (2013.01); *G01K 7/06* (2013.01); *G01N 25/72* (2013.01); *B01D 53/9445* (2013.01); *F01N 2550/02* (2013.01); *F01N 2560/06* (2013.01); *F01N 2560/14* (2013.01); *F01N 2900/08* (2013.01); *F01N 2900/1404* (2013.01)

(58) Field of Classification Search
CPC ..... F01N 2900/1404; F01N 2900/1602; F01N 2900/1621; F01N 2900/1811; F02D 2200/0802; F02D 41/1441; F02D 41/1446; G01M 15/10; G01M 15/102; G01N 25/72; Y02T 10/47; Y02T 10/44; Y02T 10/123; Y02T 10/7258
See application file for complete search history.

(56) References Cited

U.S. PATENT DOCUMENTS

| | | | | |
|---|---|---|---|---|
| 5,877,413 A | * | 3/1999 | Hamburg | F01N 11/007 60/277 |
| 5,896,743 A | * | 4/1999 | Griffin | F01N 11/002 60/274 |
| 6,079,203 A | * | 6/2000 | Wakamoto | F01N 3/2066 60/274 |
| 6,131,439 A | * | 10/2000 | Hamburg | F01N 11/007 60/276 |
| 7,305,819 B2 | | 12/2007 | Yasui | |
| 7,434,385 B2 | | 10/2008 | Ichimoto et al. | |
| 7,832,194 B2 | | 11/2010 | Ichimoto et al. | |
| 8,490,385 B2 | | 7/2013 | Miyoshi et al. | |
| 8,515,710 B2 | * | 8/2013 | Wang | F02D 41/1446 374/144 |
| 8,739,615 B2 | | 6/2014 | Tsunekawa | |
| 8,806,928 B2 | * | 8/2014 | Shibata | F01N 11/002 73/114.75 |
| 9,371,763 B2 | * | 6/2016 | LaRose, Jr. | F01N 3/2033 |
| 2002/0197721 A1 | | 12/2002 | Kinugawa | |
| 2004/0205998 A1 | * | 10/2004 | Wakao | F02M 25/12 48/198.7 |
| 2006/0117739 A1 | | 6/2006 | Ichimoto et al. | |
| 2006/0142932 A1 | | 6/2006 | Yasui | |
| 2008/0196393 A1 | | 8/2008 | Ichimoto et al. | |
| 2009/0016401 A1 | * | 1/2009 | Hamada | F23C 13/00 374/10 |
| 2009/0070003 A1 | * | 3/2009 | Thuault | F01N 3/36 701/103 |
| 2009/0107114 A1 | * | 4/2009 | Ammineni | F02D 41/0235 60/277 |
| 2009/0188240 A1 | * | 7/2009 | Suzuki | B01D 53/9445 60/286 |
| 2009/0199543 A1 | | 8/2009 | Sawada et al. | |
| 2010/0050608 A1 | * | 3/2010 | Jayachandran | F01N 11/005 60/286 |
| 2010/0293924 A1 | | 11/2010 | Harima et al. | |
| 2011/0126517 A1 | | 6/2011 | Miyoshi et al. | |
| 2013/0098146 A1 | | 4/2013 | Shibata | |
| 2013/0228008 A1 | | 9/2013 | Tsunekawa | |
| 2015/0247441 A1 | * | 9/2015 | Takita | F01N 11/005 73/114.75 |
| 2016/0161371 A1 | * | 6/2016 | Nakasone | G01M 15/102 73/114.75 |
| 2016/0161430 A1 | * | 6/2016 | Lana | F01N 11/002 73/114.75 |
| 2017/0002714 A1 | * | 1/2017 | De Smet | F01N 11/002 |
| 2018/0283248 A1 | * | 10/2018 | Upadhyay | F01N 3/2066 |

FOREIGN PATENT DOCUMENTS

| | | | | |
|---|---|---|---|---|
| CN | 101932813 A | | 12/2010 | |
| CN | 102105663 A | | 6/2011 | |
| CN | 103306792 A | | 9/2013 | |
| DE | 19850338 A1 | * | 5/2000 | ............. F01N 11/00 |
| EP | 0822323 | | 2/1998 | |
| JP | S61145824 U | | 9/1986 | |
| JP | H08303280 A | | 11/1996 | |
| JP | 2001123824 A | | 5/2001 | |
| JP | 2001271639 A | | 10/2001 | |
| JP | 2004176615 A | | 6/2004 | |
| JP | 2004-340102 A | | 12/2004 | |
| JP | 2014062510 A | | 4/2014 | |
| JP | 2017-198107 | | 11/2017 | |
| WO | 2011135710 A1 | | 11/2011 | |
| WO | WO-2011135710 A1 | * | 11/2011 | ............ F01N 11/002 |

\* cited by examiner (a)

(b)

CATALYST DETERIORATION DETECTING SYSTEM AND CATALYST DETERIORATION DETECTING METHOD

TECHNICAL FIELD

The present invention relates to a catalyst deterioration detecting system and a catalyst deterioration detecting method for an internal combustion engine.

BACKGROUND ART

Exhaust gas emitted from an internal combustion engine, such as a gasoline engine or a diesel engine, of an automobile, a motorcycle (also referred to as a saddle-type vehicle), etc., contains hazardous components such as NOx, HC, and CO. Three-way catalysts have conventionally been used to remove these hazardous components and render the exhaust gas harmless. Examples of three-way catalysts that have been used include mixtures including discretionary amounts of noble metals, such as Pt, Pd, and Rh, and alumina, ceria, zirconia, and/or composite oxides thereof.

As a part of exhaust gas regulation, the OBD-II regulation was introduced in the United States from around 1990, the regulation mandating the installation, onto a vehicle, of a system that: detects abnormalities, such as deterioration of an exhaust gas purification catalyst (hereinafter also referred to simply as "catalyst"); and, upon detection of such abnormalities by an on-board diagnostic (OBD) device, notifies the driver of the abnormality by lighting up a warning lamp on an instrument panel, and stores the failure code(s) which can be read out with a standardized scanning tool. Similar regulations have been introduced in Europe and Japan. Thus, there is a demand for an inexpensive, versatile system capable of detecting deterioration of a catalyst.

As disclosed in Patent Literatures 1 and 2, conventional catalyst deterioration detecting systems generally employ $O_2$ sensors on both the upstream and downstream sides of a catalyst, and judge deterioration of the catalyst on the basis of fluctuations in the outputs of the $O_2$ sensors. Patent Literatures 3 and 4, on the other hand, disclose techniques that do not employ $O_2$ sensors but instead include temperature detection means on both the upstream and downstream sides of a catalyst in an exhaust passage of an internal combustion engine, and detect deterioration on the basis of a difference between the temperatures detected by both means.

CITATION LIST

Patent Literature

Patent Literature 1: JP H8-303280 A
Patent Literature 2: JP 2004-176615 A
Patent Literature 3: JP 2014-62510 A
Patent Literature 4: US 2002/197721 A1

SUMMARY OF INVENTION

In general, $O_2$ sensors use platinum-coated zirconia electrolytes and are thus expensive. Thus, there is a demand for inexpensive catalyst deterioration detecting systems that do not use $O_2$ sensors, in contrast to the systems disclosed in Patent Literatures 1 and 2. As described above, Patent Literatures 3 and 4 disclose systems for detecting catalyst deterioration without using an $O_2$ sensor. Patent Literatures 3 and 4, however, merely describe the employment of a temperature difference between the upstream and downstream sides of a catalyst, and are not necessarily suitable for actual driving environments in which the accelerator and the brake are frequently used.

An objective of the invention is to provide a catalyst deterioration detecting system and a catalyst deterioration detecting method capable of overcoming the various drawbacks of the aforementioned conventional art.

The present invention provides a catalyst deterioration detecting system for detecting deterioration of a catalyst provided in an exhaust passage of an internal combustion engine, the system including:

an upstream-side temperature detection means that detects a temperature of an exhaust on an upstream side of the catalyst;

a downstream-side temperature detection means that detects a temperature of the exhaust on a downstream side of the catalyst; and either (A) a recognition unit that, during acceleration operation, recognizes a change point (T1) detected by the upstream-side temperature detection means at which the temperature changes from temperature fall or constant temperature to temperature rise and a change point (T2) detected by the downstream-side temperature detection means at which the temperature changes from temperature fall or constant temperature to temperature rise, and a determination unit that determines that the catalyst has deteriorated when a difference between the change points ($\Delta T=T2-T1$) becomes equal to or longer than a predetermined time, or (B) a recognition unit that, during deceleration operation, recognizes a change point (T1') detected by the upstream-side temperature detection means at which the temperature changes from temperature rise or constant temperature to temperature fall and a change point (T2') detected by the downstream-side temperature detection means at which the temperature changes from temperature rise or constant temperature to temperature fall, and a determination unit that determines that the catalyst has deteriorated when a difference between the change points ($\Delta T'=T2'-T1'$) becomes equal to or longer than a predetermined time.

The present invention also provides a catalyst deterioration detecting method for detecting deterioration of a catalyst provided in an exhaust passage of an internal combustion engine, the method including:

employing
an upstream-side temperature detection means that detects a temperature of an exhaust on an upstream side of the catalyst, and
a downstream-side temperature detection means that detects a temperature of the exhaust on a downstream side of the catalyst; and either (a) recognizing, during acceleration operation, a change point (T1) detected by the upstream-side temperature detection means at which the temperature changes from temperature fall or constant temperature to temperature rise and a change point (T2) detected by the downstream-side temperature detection means at which the temperature changes from temperature fall or constant temperature to temperature rise, and determining that the catalyst has deteriorated when a difference between the change points ($\Delta T=T2-T1$) becomes equal to or longer than a predetermined time, or (b) recognizing, during deceleration operation, a change point (T1') detected by the upstream-side temperature detection means at which the temperature changes from temperature rise or constant temperature to temperature fall and a change point (T2') detected by the downstream-side temperature detection means at which the temperature changes from temperature rise or constant temperature to temperature fall, and determining that the catalyst has deteriorated when a difference between the change points ($\Delta T' = T2' - T1'$) becomes equal to or longer than a predetermined time.

BRIEF DESCRIPTION OF DRAWINGS

FIG. 6(a) illustrates a chart for acceleration from 0 km/h to 32 km/h, and FIG. 6(b) illustrates a chart for acceleration from 0 km/h to 50 km/h.

DESCRIPTION OF EMBODIMENTS

The present invention is described below according to preferred embodiments thereof.

Figure 1:
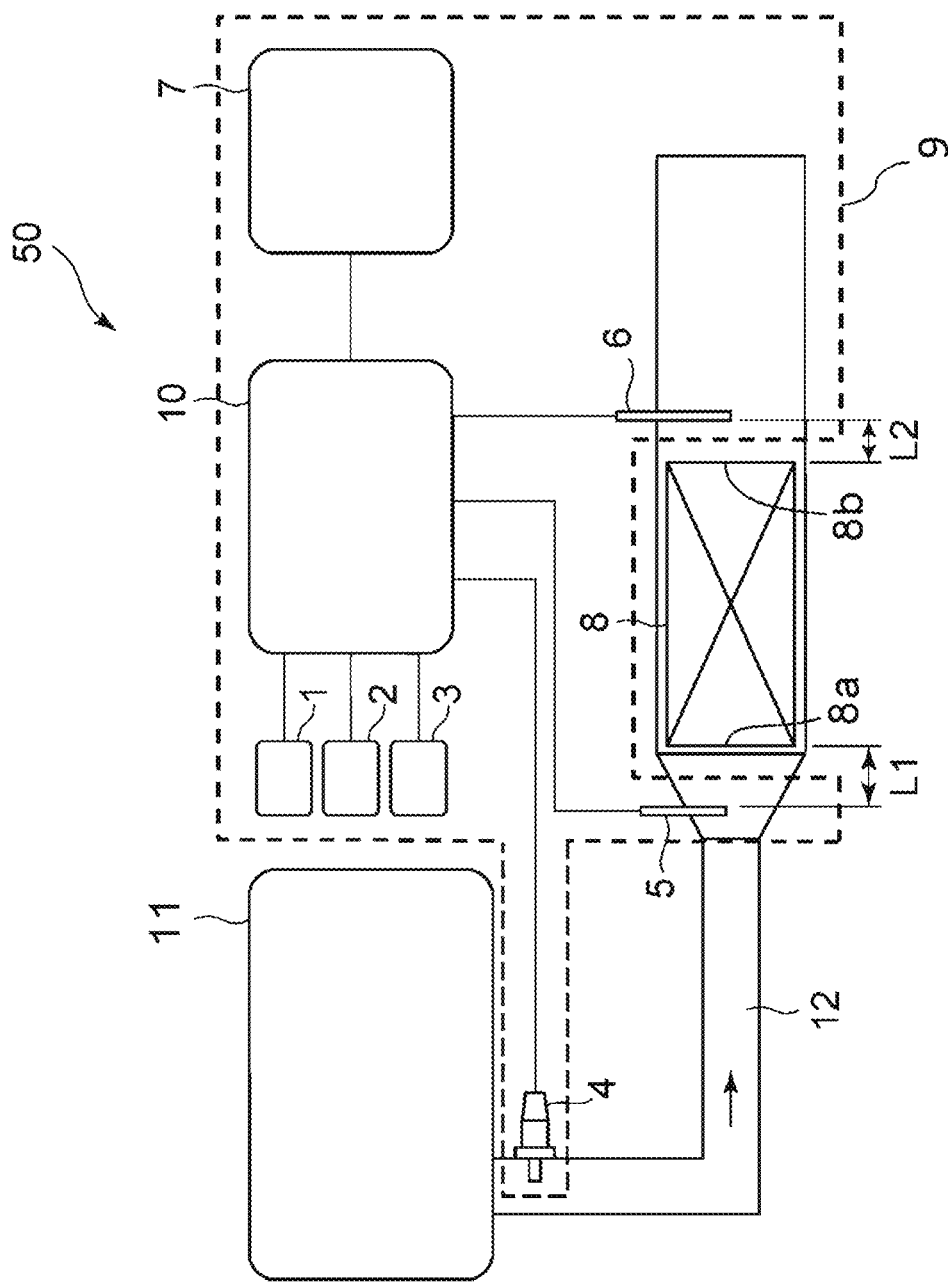
FIG. 1 is a schematic diagram illustrating an example of an overall configuration of a control system of an internal combustion engine.

FIG. 1 illustrates a control system 50 of an internal combustion engine equipped with a catalyst deterioration detecting system 9 according to the present embodiment. An example of the control system 50 is a control system of an engine of a vehicle. The control system 50 illustrated in FIG. 1 includes an engine 11, and an exhaust pipe 12 that guides exhaust gas from the engine 11 to the exterior. A catalyst 8 is provided midway of the exhaust pipe 12. The shape of the exhaust pipe 12 is not limited; for example, the exhaust pipe may have, at a position upstream of where the catalyst 8 is provided, an increasing-diameter portion whose diameter increases toward the catalyst 8, as illustrated in FIG. 1. The catalyst 8 is an oxidation catalyst that oxidizes carbon monoxide (CO) and hydrocarbons (HC) in the exhaust gas of the engine 11 and purifies them into carbon dioxide and water, and more preferably, is a three-way catalyst that simultaneously performs reduction of NOx into nitrogen together with the oxidation. An example of the catalyst is a powder including, in combination, noble metals, such as Pt, Pd, and Rh, and alumina, ceria, zirconia, and/or composite oxides thereof. The powder is usually employed as a catalyst layer supported on a catalyst support. The catalyst support is made, for example, of ceramic or a metal material. The shape of the catalyst support is not particularly limited; in general, the catalyst support is shaped, for example, into a honeycomb configuration, a plate, pellets, a DPF, or a GPF, and is preferably a honeycomb, a DPF, or a GPF. Examples of materials for the catalyst support include ceramics, such as alumina ($Al_2O_3$), mullite ($3Al_2O_3 \cdot 2SiO_2$), cordierite ($2MgO \cdot 2Al_2O_3 \cdot 5SiO_2$), aluminum titanate ($Al_2TiO_5$), and silicon carbide (SiC), and metal materials such as stainless steel.

The catalyst deterioration detecting system 9 of the present embodiment illustrated in FIG. 1 includes: an upstream-side temperature detection means 5 that detects a temperature on the upstream side of the catalyst 8 in the exhaust passage (the exhaust pipe 12 in the example illustrated in FIG. 1); a downstream-side temperature detection means 6 that detects a temperature on the downstream side of the catalyst 8 in the exhaust passage (the exhaust pipe 12 in the example illustrated in FIG. 1); and an engine control unit (ECU) 10 that recognizes change points T1 and T1' in temperatures detected by the upstream-side temperature detection means 5 and change points T2 and T2' in temperatures detected by the downstream-side temperature detection means 6, and determines deterioration of the catalyst on the basis of the change points. Temperature sensors can be used for the upstream-side temperature detection means 5 and the downstream-side temperature detection means 6. Concrete examples of temperature sensors include thermocouples and temperature measurement resistors. In FIG. 1, the upstream-side temperature detection means 5 is provided on the upstream side of the catalyst 8 in the exhaust pipe 12, and the downstream-side temperature detection means 6 is provided on the downstream side of the catalyst 8 in the exhaust pipe 12. It is preferable that, in a cross section orthogonal to the length direction of the exhaust pipe 12, the upstream-side temperature detection means 5 and the downstream-side temperature detection means 6 are provided so as to be able to detect the temperature at substantially the central portion in the cross section. Herein, it is sufficient if "substantially the central portion in the cross section" is in a range within two-thirds, preferably one-third, of the distance from the center of the exhaust pipe to the inner surface of the exhaust pipe in the aforementioned cross section. In cases where the cross section of the exhaust pipe is circular, the center of the exhaust pipe in the aforementioned cross section refers to the center of the circle, and in cases where the exhaust pipe is not circular, the center of the exhaust pipe refers to the center of the largest circle that can be rendered inside the cross section. Note that, hereinbelow, the "cross section of the exhaust pipe 12" refers to the cross section orthogonal to the length direction of the exhaust pipe 12, unless specifically stated otherwise.

In the engine control system 50 of FIG. 1, the intake pressure of the engine, the engine rotation speed, the throttle opening angle, and the air-fuel ratio are detected respectively by a Ph sensor 1, an Ne sensor 2, a Th sensor 3, and an $O_2$ sensor 4, and are controlled by the engine control unit (ECU) 10. As illustrated in FIG. 1, the Pb sensor 1, the Ne sensor 2, the Th sensor 3, and the $O_2$ sensor 4 may be included in the catalyst deterioration detecting system 9.

The catalyst deterioration detecting system 9 of the present embodiment is provided in a device including an internal combustion engine, such as a transportation means, e.g., a vehicle, an airplane or a ship, or a power generator, as a part of the control system 50 of the internal combustion engine illustrated in FIG. 1. The catalyst deterioration detecting system 9 detects catalyst deterioration on the basis of an interval between the times, respectively on the upstream and downstream sides of the catalyst 8, at which the inclination of the detected temperature is inverted during acceleration operation or deceleration operation of the internal combustion engine. It should be noted that, herein, "inverted" includes cases where the inclination changes from positive to negative and cases where the inclination changes from negative to positive, and also includes cases where the inclination changes from zero to positive or negative. During acceleration operation of a transportation means such as a vehicle (for example, an increase in the movement speed (km/h) of the transportation means), the internal combustion engine will undergo acceleration operation (for example, an increase in the rotation speed (rpm) of an engine shaft). Similarly, during deceleration operation of a vehicle (for example, a decrease in the movement speed (km/h) of the transportation means), the internal combustion engine will undergo deceleration operation (for example, a decrease in the rotation speed (rpm) of an engine shaft). Thus, when installed on a transportation means such as a vehicle, the catalyst deterioration detecting system 9 of the present embodiment can detect catalyst deterioration on the basis of an interval between the times at which the inclination of the respective temperatures detected respectively by the upstream-side temperature detection means 5 and the downstream-side temperature detection means 6 is inverted during acceleration operation or deceleration operation of the transportation means. Preferably, "acceleration operation of a transportation means" refers, for example in cases of a vehicle, to an acceleration of 0.52 m/sec$^2$ or greater, or an acceleration in which the speed difference before and after acceleration is 30 km/h or greater. Preferably, "deceleration operation of a transportation means" refers, for example in cases of a vehicle, to a deceleration of 0.52 m/sec$^2$ or greater, or a deceleration in which the speed difference before and after deceleration is 20 km/h or greater.

Figure 2:
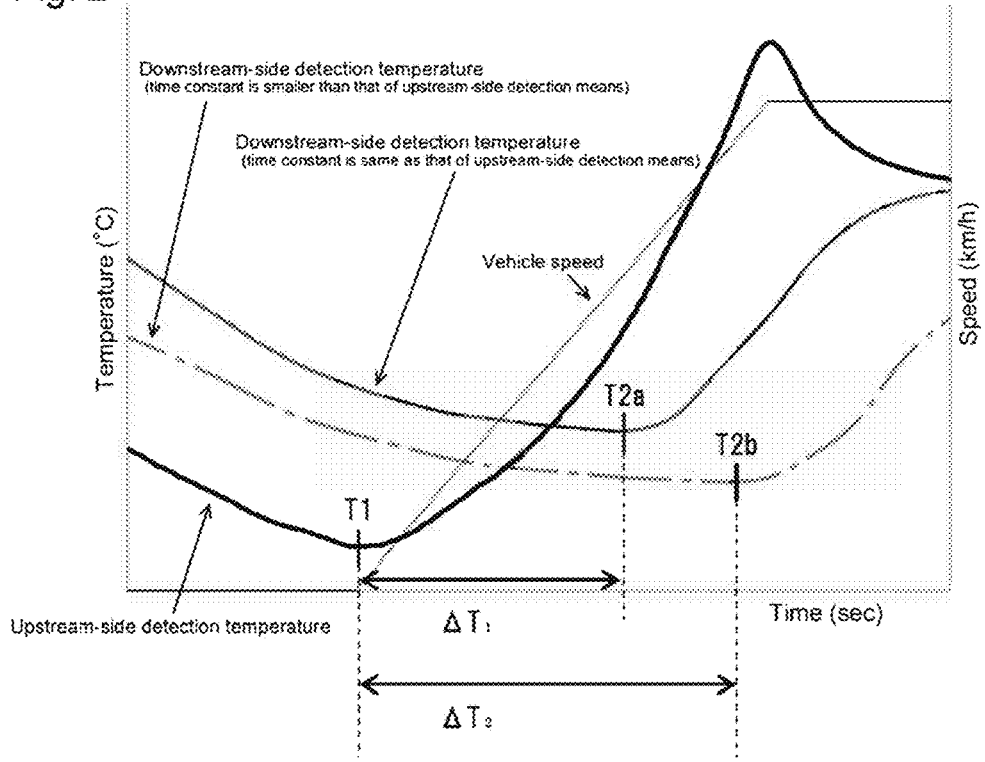
FIG. 2 is an example of a chart plotting a change in vehicle speed during acceleration operation of a vehicle equipped with a catalyst deterioration detecting system of the invention, and a change in temperature detected by each temperature detection means.

FIG. 2 illustrates an example plotting a change in vehicle speed during acceleration operation of a transporting means equipped with the catalyst deterioration detecting system 9 (and the internal combustion engine's control system 50 including the same) of the present embodiment, and a change in temperature detected by the upstream-side temperature detection means 5 and the downstream-side temperature detection means 6. As illustrated in FIG. 2, during acceleration operation of the transportation means, the temperature of the exhaust gas increases along with the acceleration operation of the internal combustion engine, and thus, the temperature detected by the upstream-side temperature detection means 5 immediately changes from temperature fall or constant temperature to temperature rise, to give a change point T1 from temperature fall or constant temperature to temperature rise. On the other hand, the temperature detected by the downstream-side temperature detection means 6 changes from temperature fall or constant temperature to temperature rise in a delayed manner compared to the upstream-side temperature detection means, to give a change point T2$a$ or T2$b$. This delay not only reflects the distance between the engine 11 and the downstream-side temperature detection means 6, but also reflects the fact that the oxidation reaction caused by the catalyst 8, which occurs as a result of the catalyst 8 coining into contact with the exhaust gas, is an exothermic reaction. Inventors have found that the greater the degree of catalyst deterioration, the further delayed the occurrence of the change from temperature fall or constant temperature to temperature rise at the downstream-side temperature detection means 6 becomes, and that this can be employed to detect deterioration of the catalyst. This is thought to be because, the further the deterioration of the catalyst progresses, the more the oxidation reaction of HC and CO by the catalyst is delayed.

Figure 3:
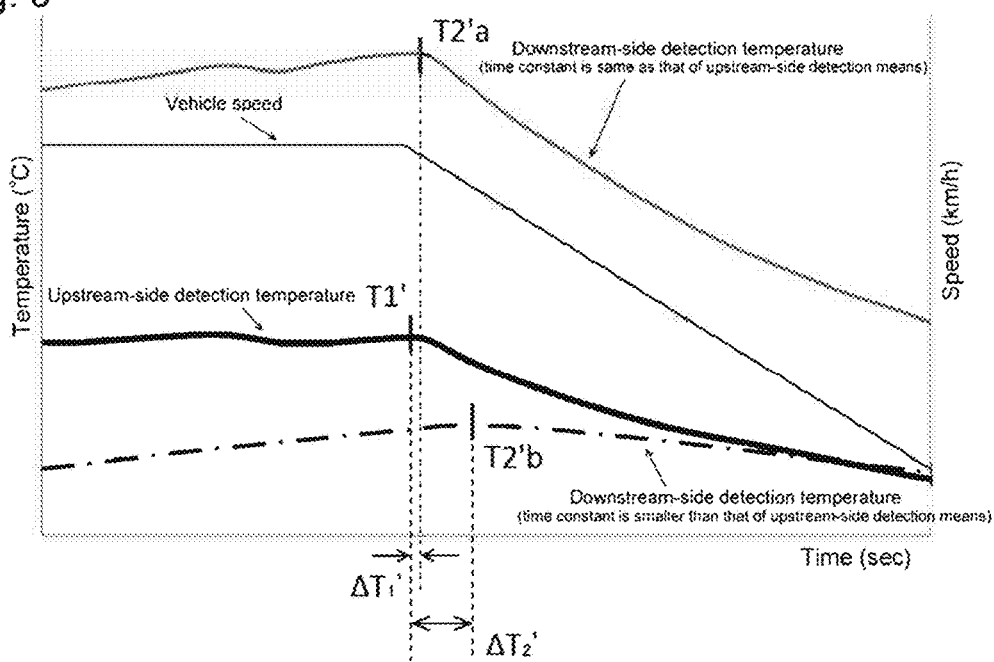
FIG. 3 is an example of a chart plotting a change in vehicle speed during deceleration operation of a vehicle equipped with a catalyst deterioration detecting system of the invention, and a change in temperature detected by each temperature detection means.

Similarly, also during deceleration operation of the transportation means, deceleration operation of the internal combustion engine occurs, and thus, the temperature falls from temperature rise or constant temperature at the upstream-side temperature detection means 5 and the downstream-side temperature detection means 6. FIG. 3 illustrates an example plotting a change in vehicle speed during deceleration operation of a transporting means equipped with the catalyst deterioration detecting system 9 (and the internal combustion engine's control system 50 including the same) of the present embodiment, and a change in temperature detected by each of the temperature detection means. As illustrated in FIG. 3, during deceleration operation of the transportation means, the temperature of the exhaust gas decreases along with the deceleration operation of the internal combustion engine, and thus, the upstream-side temperature detection means 5 detects a change point T1' from temperature rise or constant temperature to temperature fall. On the other hand, the downstream-side temperature detection means 6 detects a change point T2'$a$ or T2'$b$ from temperature rise or constant temperature to temperature fall in a delayed manner compared to the upstream-side temperature detection means. Here, the greater the degree of deterioration of the catalyst 8, the further delayed the change from temperature rise or constant temperature to temperature fall at the downstream-side temperature detection means 6 becomes, compared to the change from temperature rise or constant temperature to temperature fall at the upstream-side temperature detection means 5. Thus, similar to the time of acceleration operation, deterioration of the catalyst can be detected by employing the difference $\Delta T'$ between the change points T1' and T2'.

Figure 4:
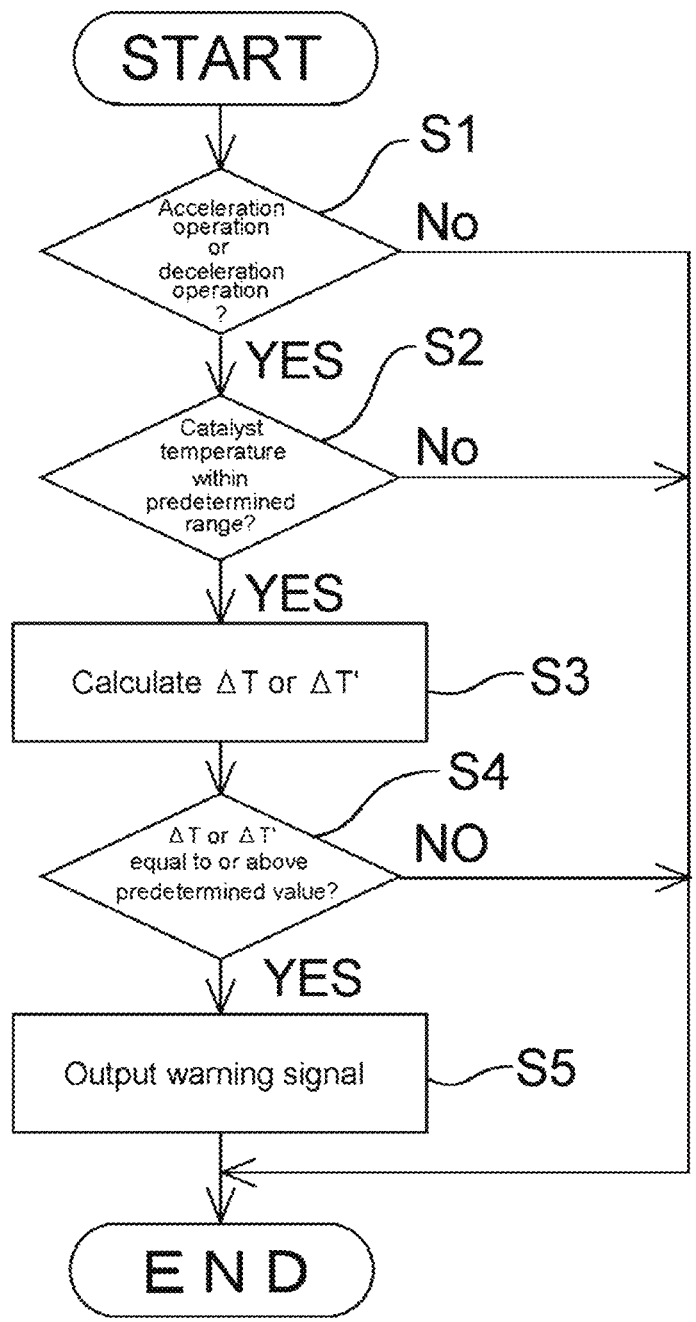
FIG. 4 is a flowchart illustrating an example of a process carried out by a catalyst deterioration detecting system and a catalyst deterioration detecting method of the invention.

An example of detecting deterioration according to the present embodiment is described according to the flowchart of FIG. 4.

As illustrated in FIG. 4, step 1 determines whether or not an internal combustion engine, or a transportation means etc. equipped therewith, is performing acceleration operation or deceleration operation. This determination is performed, for example, by detecting the rotation speed of the engine shaft with the Ne sensor 2, and, on the basis of this information, making the determination by the ECU 10. The ECU 10 is constituted by arithmetic processing means including a CPU, a memory, etc. If Yes, the flow advances to step 2, in which the temperature of the catalyst 8 is measured and it is determined by the ECU 10 whether or not the temperature of the catalyst 8 is within a predetermined range. When the temperature of the catalyst 8 is equal to or above a given value, it is considered that the oxidation reaction upon contact with the exhaust gas has occurred sufficiently, which can facilitate the determination of $\Delta T$. The temperature range of the catalyst 8 to be set as the predetermined range in step 2 is preferably from 300° C. to 600° C., more preferably from 400° C. to 500° C. The temperature of the catalyst 8 may be measured with the downstream-side temperature detection means 6, or may be measured with a separate temperature detection means inserted into the catalyst 8. As described above, the recognition unit and the determination unit of the invention may be a single control device.

Examples of instances in which an internal combustion engine, as well as transportation means etc. equipped therewith, performs acceleration operation in step 1 in a state where the catalyst 8 has been heated to a given temperature as described above include the following: when the internal combustion engine is an engine of a vehicle, an instance in which the vehicle speed is increased from a state where the vehicle is traveling at a constant speed; and an instance in which the vehicle speed is increased from an idling state or a state where the vehicle speed is decreasing. Examples of instances in which an internal combustion engine, as well as transportation means etc. equipped therewith, performs deceleration in step 1 in a state where the catalyst 8 has been heated to a given temperature include the following: when the internal combustion engine is an engine of a vehicle, an instance in which the vehicle speed is decreased from a state where the vehicle is traveling at a constant speed or a state where the vehicle speed is increasing.

If it is determined Yes in step 2, the flow advances to step 3. If it was determined in step 1 that acceleration operation is being performed, then the ECU 10 recognizes the change point T1 in temperature detected by the upstream-side temperature detection means 5 and the change point T2 in temperature detected by the downstream-side temperature detection means 6, and calculates $\Delta T$ (=T2−T1). On the other hand, if it was determined in step 1 that deceleration operation is being performed, then the ECU recognizes the change point T1' in temperature detected by the upstream-side temperature detection means 5 and the change point T2' in temperature detected by the downstream-side temperature detection means 6, and calculates $\Delta T'$ (=T2'−T1').

The conditions for recognizing whether or not a change has occurred from temperature fall or constant temperature to temperature rise can be set as appropriate to conditions with which deterioration detection can be performed efficiently. As regards recognition of a change point from temperature fall or constant temperature to temperature rise, for example, in cases where the measurement is performed at intervals of 0.1 seconds, a point at which an increase in measured temperature of at least 0.1° C. compared to the immediately-previous temperature measurement history of the upstream-side temperature detection means 5 has occurred three consecutive times is recognized as the change point T1, and likewise, a point at which an increase in measured temperature of at least 0.1° C. compared to the immediately-previous temperature measurement history of the downstream-side temperature detection means 6 has occurred three consecutive times is recognized as the change point T2. Recognition of a change point from temperature rise or constant temperature to temperature fall is performed similarly; for example, in cases where the measurement is performed at intervals of 0.1 seconds, a point at which a decrease in measured temperature of at least 0.1° C. compared to the immediately-previous temperature measurement history of the upstream-side temperature detection means 5 has occurred three consecutive times is recognized as the change point T1', and likewise, a point at which a decrease in measured temperature of at least 0.1° C. compared to the immediately-previous temperature measurement history of the downstream-side temperature detection means 6 has occurred three consecutive times is recognized as the change point T2'.

Next, in step 4, the ECU 10 determines whether or not $\Delta T$ or $\Delta T'$ calculated in step 3 is equal to or greater than a predetermined value. If Yes, in step 5, the ECU 10 outputs a signal for displaying a warning on a monitor 7. Note that, in cases where steps 1, 2, and 4 are No, the flow is ended, and the same flow is resumed after the lapse of a predetermined period of time. The predetermined value serving as the determination criterion may be set discretionarily to a value suitable for the concrete configuration of the system.

Returning to FIG. 2, the catalyst deterioration detecting system and catalyst deterioration detecting method of the present embodiment are described in further detail. Inventors have studied methods for improving deterioration detection sensitivity at the time of detecting catalyst deterioration by employing the aforementioned $\Delta T$, and arrived at making respective time constants of the upstream-side temperature detection means and the downstream-side temperature detection means different from one another. The time constant is an index of the response speed of the temperature detection means with respect to the temperature rise or temperature fall of the surrounding environment. As illustrated in FIG. 2, Inventors have found that, in cases where the time constant of the downstream-side temperature detection means 6 is smaller (i.e., the absolute value of the time constant is smaller) than that of the upstream-side temperature detection means 5, the change (change point T2$b$) from temperature fall or constant temperature to temperature rise is delayed compared to the aforementioned change (change point T2$a$) for when the downstream-side temperature detection means has the same time constant as the upstream-side temperature detection means 5, and thus, $\Delta T$ can be prolonged. Also, from further studies, Inventors have found that, by actually making the respective time constants of the upstream-side temperature detection means 5 and the downstream-side temperature detection means 6 different from one another, the efficiency for detecting, catalyst deterioration can be improved effectively. It is more preferable to make the time constant of the downstream-side temperature detection means smaller than the time constant of the upstream-side temperature detection means, from the viewpoint of increasing the change of the change point and being able to make $\Delta T$ longer.

The same applies to deceleration operation as illustrated in FIG. 3; in cases where the time constant of the downstream-side temperature detection means 6 is smaller the absolute value of the time constant is smaller) than that of the upstream-side temperature detection means 5, the change (change point T2'$b$) from temperature rise or constant temperature to temperature fall is delayed compared to the aforementioned change (change point T2'$a$) for when the downstream-side temperature detection means has the same time constant as the upstream-side temperature detection means 5, and thus, $\Delta T'$ can be prolonged.

In the present embodiment, the time constants of the upstream-side temperature detection means 5 and the downstream-side temperature detection means 6 differ depending on whether the surrounding environment is undergoing temperature rise or temperature fall, and can be measured as follows.

The time constant during temperature rise is found as follows. In a 245-mm-long stainless steel exhaust pipe having a cross-sectional area of 21.06 cm$^2$ and through which a 450° C. exhaust gas flows at a flow rate of 5 L/sec, each temperature detection means, which is in a state detecting 25° C., is set to a central portion, in the length direction, of the exhaust pipe so as to detect the temperature at the central portion in the cross section of the exhaust pipe. A chart is obtained by plotting the temperature change of the temperature detection means at intervals of 0.1 seconds up to 405° C. The chart is subjected to linear regression, and the inclination (unit: ° C./sec) of the obtained linear function/straight line is found as the time constant during temperature rise.

On the other hand, the time constant during temperature fall is found as follows. Each temperature detection means is set at a central portion, in the length direction, of a 245-mm-long stainless steel exhaust pipe having a cross-sectional area of 21.06 cm$^2$ and through which an exhaust gas giving a detection temperature of 450° C. flows at a flow rate of 5 L/sec. From this state, the temperature detection means is set in the atmosphere having a temperature of 25° C. and an air velocity of 16.7 m/sec, to obtain a chart plotting the temperature change of the temperature detection means at intervals of 0.1 seconds down to 30° C. The chart is subjected to linear regression, and the inclination (unit: ° C./sec) of the obtained linear function/straight line is found as the time constant during temperature fall. The exhaust gas used for measuring the time constants in the Examples is used as the exhaust gas for measuring the aforementioned time constants.

When the ratio, $t_{\beta-r}/t_{\alpha-r}$, between the time constant of the upstream-side temperature detection means 5 during temperature rise (referred to hereinafter also as "time constant $t_{\alpha-r}$") and the time constant of the downstream-side temperature detection means 6 during temperature rise (referred to hereinafter also as "time constant $t_{\beta-r}$") is equal to or above a given value, the deterioration detection sensitivity can be further improved, whereas setting the ratio to equal to or below a given value facilitates ensuring the ease of deriving the change points for both the upstream-side temperature detection means 5 and the downstream-side temperature detection means 6. From these viewpoints, the ratio $t_{\beta-r}/t_{\alpha-r}$ is preferably from 0.15 to 0.85, more preferably from 0.25 to 0.80, even more preferably from 0.25 to 0.50. The time constant $t_{\alpha-r}$ of the upstream-side temperature detection means 5 during temperature rise is preferably 20.0° C./sec or greater, more preferably 27.0° C./sec or greater. The time constant $t_{\beta-r}$ of the downstream-side temperature detection means 6 during temperature rise is preferably from 5.0° C./sec to 11.5° C./sec, more preferably from 7.0° C./sec to 7.5° C./sec.

When the ratio, $t_{\beta-1}/t_{\alpha-1}$, between the time constant of the upstream-side temperature detection means 5 during temperature fall (referred to hereinafter also as "time constant $t_{\alpha-1}$") and the time constant of the downstream-side temperature detection means 6 during temperature fall (referred to hereinafter also as "time constant $t_{\beta-1}$") is equal to or above a given value, the deterioration detection sensitivity can be further improved, whereas setting the ratio to equal to or below a given value facilitates ensuring the ease of deriving the change points for both the upstream-side temperature detection means 5 and the downstream-side temperature detection means 6. From these viewpoints, the ratio $t_{\beta-1}/t_{\alpha-1}$ is preferably from 0.05 to 0.70, more preferably from 0.25 to 0.65, even more preferably from 0.25 to 0.45. The time constant $t_{\alpha-1}$ of the upstream-side temperature detection means 5 during temperature fall is preferably −16.0° C./sec or less, more preferably −26° C./sec or less. The time constant $t_{\beta-1}$ of the downstream-side temperature detection means 6 during temperature fall is preferably from −9.0° C./sec to −2.0° C./sec, more preferably from −7.7° C./sec to −7.2° C./sec.

From the viewpoint of increasing detection frequency, the respective absolute values of the time constants during temperature rise and temperature fall are preferably both within a range from 2.0 to 25.0, more preferably within a range from 5.0 to 20.0, and particularly, it is preferably within a range from 5.5 to 8.5 from the viewpoint of maximizing the frequency of detecting ΔT.

Methods for making the time constants different between the upstream-side temperature detection means 5 and the downstream-side temperature detection means 6 include, for example: a method of using sheathed thermocouples for the upstream-side temperature detection means 5 and the downstream-side temperature detection means 6 and using different materials for the sheathed thermocouples; a method of making the sheath diameters different; and a method of attaching, to the outer circumference of the sheathed thermocouple, a barrier material having a thermal conductivity different from the thermal conductivity of the sheathed thermocouple. With these methods, it is possible to easily achieve detection means having different time constants for the upstream-side temperature detection means 5 and the downstream-side temperature detection means 6, and thus, it is possible to easily achieve an inexpensive and highly versatile catalyst deterioration detecting system having a high deterioration detection sensitivity.

A known type of sheathed thermocouple is made by joining two different types of bare wires at their tip ends, and measures the temperature by employing the Seebeck effect, in which a thermoelectromotive force occurs in the closed circuit, and thereby a current flows through the circuit, when a temperature difference occurs between the two junctions. The junction on the temperature-measuring side is called the measuring junction. The sheathed thermocouple is made by housing the thermocouple bare wires in a sheath, which is a protection tube, and integrating the wires and the sheath by filling and sealing the sheath with an insulating material.

The sheathed thermocouple may be a JIS-compliant thermocouple or a thermocouple not compliant with JIS, but is preferably a thermocouple capable of supporting exhaust temperatures of around 200° C. to 800° C. from an internal combustion engine, and examples include Chromel-Alumel (K) thermocouples, platinum-platinum/rhodium (R) thermocouples, and Nicrosil-Nisil (N) thermocouples. A preferred material for the sheath is metal, with examples including stainless steel (e.g., SUS 316, SUS 310S, SUS 347) and chromium-nickel alloys (NCF 600). An example of an inorganic insulating material is magnesium oxide (MgO). The length of the sheathed thermocouple is not limited, but is generally from 0.15 m to 0.5 m, for example. In cases of using sheathed thermocouples for the upstream-side and downstream-side temperature detection means, the types, materials, etc., may be the same, or may be different from one another.

In cases where the cross section of the sheath (the cross section orthogonal to the sheath's length direction) at the measuring junction in the length direction of the sheath is circular, the sheath diameter refers to the outer diameter (the outer-side diameter) at the measuring junction. In cases where the cross section is not circular, the sheath diameter refers to the equivalent circle diameter of an area of a portion (including the sheath's wall thickness) that is present inside the sheath's outer shape at the aforementioned cross section. The wall thickness of the sheath is not particularly limited, and is set in accordance with the sheath diameter; in cases of two types of sheathed thermocouples having different sheath diameters, the thermocouple having a greater sheath diameter often has a greater wall thickness.

In cases of making the sheath diameters of the sheathed thermocouples different, it is preferable that the sheath diameter of the sheathed thermocouple used for the downstream-side temperature detection means 6 greater than the sheath diameter of the sheathed thermocouple used for the upstream-side temperature detection means 5 from the viewpoint of effectively improving the sensitivity for detecting catalyst deterioration. More specifically, when φ1 is defined as the sheath diameter of the sheathed thermocouple used as the upstream-side temperature detection means 5 and φ2 is defined as the sheath diameter of the sheathed thermocouple used as the downstream-side temperature detection means 6, it is preferable that the ratio φ2/φ1 between φ1 and φ2 is greater than 1 and preferably 4.5 or less, and more preferably from 2.0 to 4.0 from the viewpoint of particularly improving detection sensitivity.

The sheath diameter of the sheathed thermocouple is not particularly limited so long as it provides the aforementioned preferable time constant. For example, the sheath diameter φ1 is preferably 1.6 mm or greater from the viewpoint of durability such as corrosion resistance, and preferably 2.3 mm or less from the viewpoint of easily improving deterioration detection sensitivity because ΔT can be increased easily. On the other hand, the sheath diameter φ2 is preferably 2.3 mm or greater from the viewpoint of durability such as corrosion resistance and from the viewpoint of easily improving deterioration detection sensitivity because ΔT can be increased easily, and the sheath diameter φ2 is preferably 4.8 mm or less from the viewpoint of easily improving deterioration detection sensitivity because T2 is easy to detect.

In the exhaust passage (exhaust pipe 12) of the engine 11, it is preferable that the ratio L2/L1 between a distance L1 (see FIG. 1) from an inlet-side end portion 8a of the catalyst 8 to a temperature detection position of the upstream-side temperature detection means 5 and a distance L2 (see FIG. 1) from an outlet-side end portion 8b of the catalyst 8 to a temperature detection position of the downstream-side temperature detection means 6 is preferably 0.18 or greater from the viewpoint of easily improving deterioration detection sensitivity by being able to make ΔT (or ΔT') greater than a given value and from the viewpoint of freedom in layout, and is preferably 5.00 or less from the viewpoint of ease of detecting T2 (or T2') and from the viewpoint of freedom in layout. From these viewpoints, L2/L1 is preferably from 0.18 to 5.00, more preferably from 0.5 to 3.0. The "inlet-side" refers to the side of the inlet of the exhaust in the exhaust passage 12, and the "outlet-side" refers to the side of the outlet of the exhaust in the exhaust passage 12.

Although it depends on the type of internal combustion engine and the type of catalyst (e.g., the composition and ratio of noble metals used, the catalyst material, the length and diameter of the catalyst), L1 is preferably from 20 to 400 mm, more preferably from 20 to 110 mm, from the viewpoint of detecting T1 (or T1') accurately from exhaust heat and improving catalyst deterioration detection sensitivity. L2 is preferably from 20 to 100 mm, more preferably from 20 to 70 mm, from the viewpoint of improving catalyst deterioration detection sensitivity and detecting T2 (or T2') accurately.

Examples of usable internal combustion engines include gasoline engines, diesel engines, hybrid engines, and engines using fuels such as natural gas, ethanol, and dimethyl ether. Among the above, gasoline engines are preferred, because the exhaust gas has a large heat quantity and thus determination of deterioration detection based on ΔT (or ΔT') is easy.

The catalyst deterioration detecting system and catalyst deterioration detecting method of the present embodiment described above are suitably applicable for detecting deterioration of an exhaust-gas purifying catalyst for purifying exhaust gas emitted from an engine of, for example, an automobile or a motorcycle (saddle-type vehicle) by making use of the low cost, versatility, and deterioration detection sensitivity of the system/method.

EXAMPLES

The invention is described in further detail below according to Examples. The scope of the invention, however, is not limited to the following Examples.

Reference Examples 1 to 6: Measurement of Time Constant

Sheathed thermocouples (all products of Nikkato Corporation) respectively having sheath diameters as described in Table 1 below were used. Each sheathed thermocouple which was at 25° C. was inserted to a center, in the length direction, of an exhaust pipe (length: 245 mm) having a cross-sectional area of 21.06 cm² and made of stainless steel (SUS 304) and through which a 450° C. exhaust gas flows at a flow rate of 5 L/sec, so as to detect the temperature at the central portion, in the cross section, of the exhaust pipe, and the temperature detected by the thermocouple was plotted up to 405° C. at intervals of 0.1 seconds. Also, each sheathed thermocouple which was at 450° C. was set in an atmospheric environment having a temperature of 25° C. and an air velocity of 16.7 m/sec, and the temperature detected by the thermocouple was plotted down to 30° C. at intervals of 0.1 seconds.

The time-to-temperature chart obtained for each Reference Example was subjected to linear regression with calculation software (Excel ver. 2010). The inclination of the linear function was found as the time constant and is shown in Table 1. The exhaust gas used above had the following composition in terms of volume: 100 ppm CO; 15.0% $CO_2$; 50 ppm THC; 0.01% or less $O_2$; 50 ppm $NO_X$; and $N_2$ as the balance.

TABLE 1

| | Sheath diameter (mm) | Time constant during temperature rise (° C./sec) | Time constant during temperature fall (° C./sec) |
| --- | --- | --- | --- |
| Reference Example 1 | φ1.6 | 27.79 | −26.35 |
| Reference Example 2 | φ2.3 | 21.52 | −16.30 |
| Reference Example 3 | φ3.2 | 11.08 | −8.99 |
| Reference Example 4 | φ4.8 | 7.21 | −7.41 |
| Reference Example 5 | φ6.4 | 6.48 | −5.83 |
| Reference Example 6 | φ8.0 | 5.46 | −2.30 |

Reference Example 7: Preparation of Deteriorated Catalyst

Figure 5:
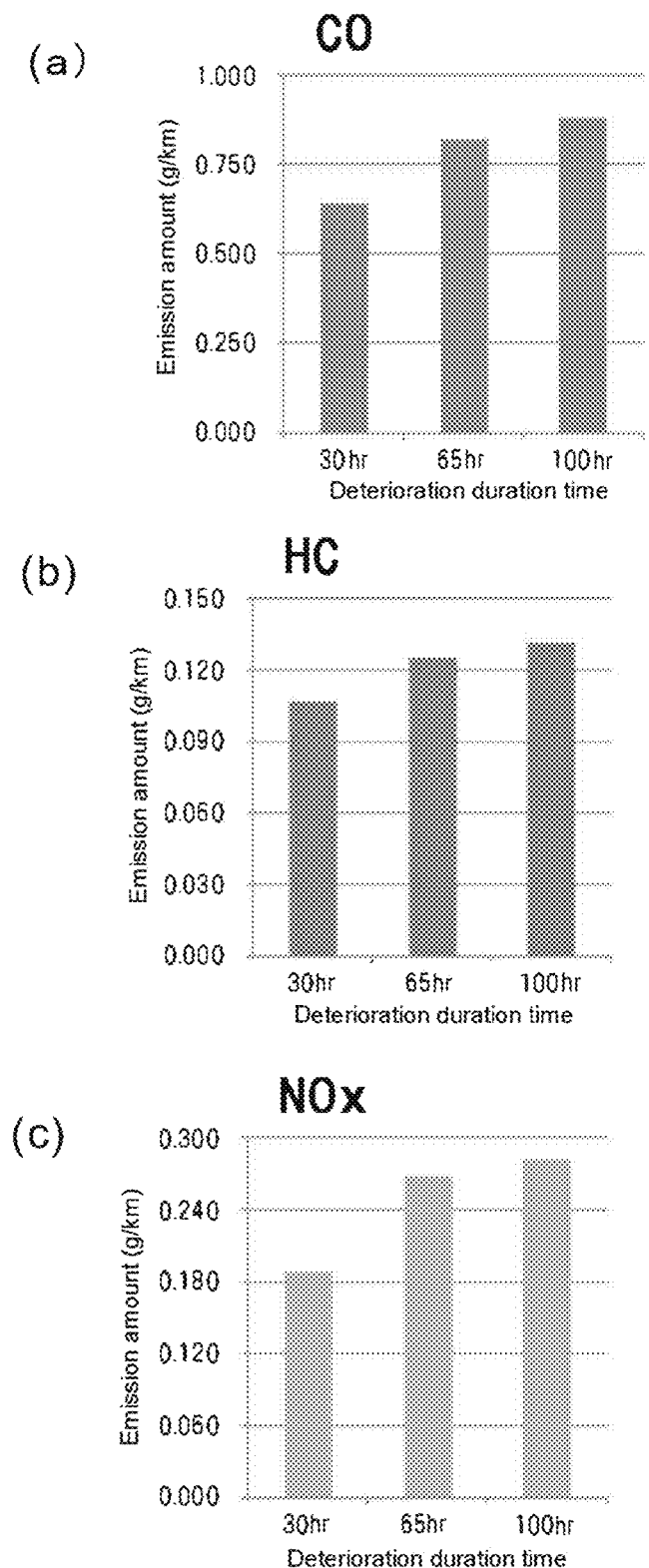
FIG. 5(a) illustrates the CO emission amounts of deteriorated catalysts used for evaluation in the Examples.
FIG. 5(b) illustrates the HC emission amounts of the deteriorated catalysts.
FIG. 5(c) illustrates the NOx emission amounts of the deteriorated catalysts.

Test catalysts 8 were each prepared by subjecting a three-way catalyst (product of Mitsui Mining & Smelting Co., Ltd.) to a deterioration treatment by setting the catalyst in an engine bench either for 30 hours, 65 hours or 100 hours at a catalyst temperature of 900° C. or higher. Each of these deteriorated catalysts, which have undergone different lengths of deterioration treatment time (also referred to as "deterioration duration time"), was attached to a catalyst-setting position in the exhaust pipe downstream of a gasoline engine of a vehicle, and in this state, the engine was subjected test drive. The emission amount (g/km) of each of CO, HC, and NOx emitted from the exhaust outlet of the exhaust pipe was measured. AIA-720 (product of Horiba, Ltd.) was used for CO measurement, FIA-720 (product of Horiba, Ltd.) was used for HC measurement, and CIA-720A (product of Horiba, Ltd.) was used for NOx measurement. The respective emission amounts of CO, NC, and NOx with respect to the catalysts' respective deterioration duration time are shown in FIG. 5.

Example 1

An engine control system 50, including the catalyst deterioration detecting system 9 of the present embodiment, was installed for catalyst deterioration detection to a saddle-type vehicle equipped with a gasoline engine. The deteriorated catalysts (after measuring the amount of exhaust gas in Reference Example 7) each having different lengths of deterioration duration time were each installed as the catalyst 8 to the system 50. For the upstream-side temperature detection means 5 and the downstream-side temperature detection means 6, sheathed thermocouples having a sheath diameter of 1.6 mm used in Reference Example 1 were used. The upstream-side temperature detection means 5 was set such that its temperature detection position was at a position in the exhaust pipe so as to be separated by 20 mm toward the upstream side from the inlet-side end portion 8a of the catalyst 8. The downstream-side temperature detection means 6 was set such that its temperature detection position was at a position so as to be separated by 60 mm toward the downstream side from the outlet-side end portion 8b of the catalyst 8.

Examples 2 to 6

For each Example, systems using three types of deteriorated catalysts having undergone different lengths of deterioration duration time were prepared in the same manner as in Example 1, except that thermocouples respectively having sheath diameters of 2.3 mm, 3.2 mm, 4.8 mm, 6.4 mm, or 8.0 mm (the thermocouples used in Reference Examples 2 to 6) were used for the downstream-side temperature detection means 6. The correspondence between the Examples and the sheath diameters of the downstream-side temperature detection means 6 is as illustrated in FIGS. 6(a) and 6(b).

{Evaluation 1-1}

Figure 6:
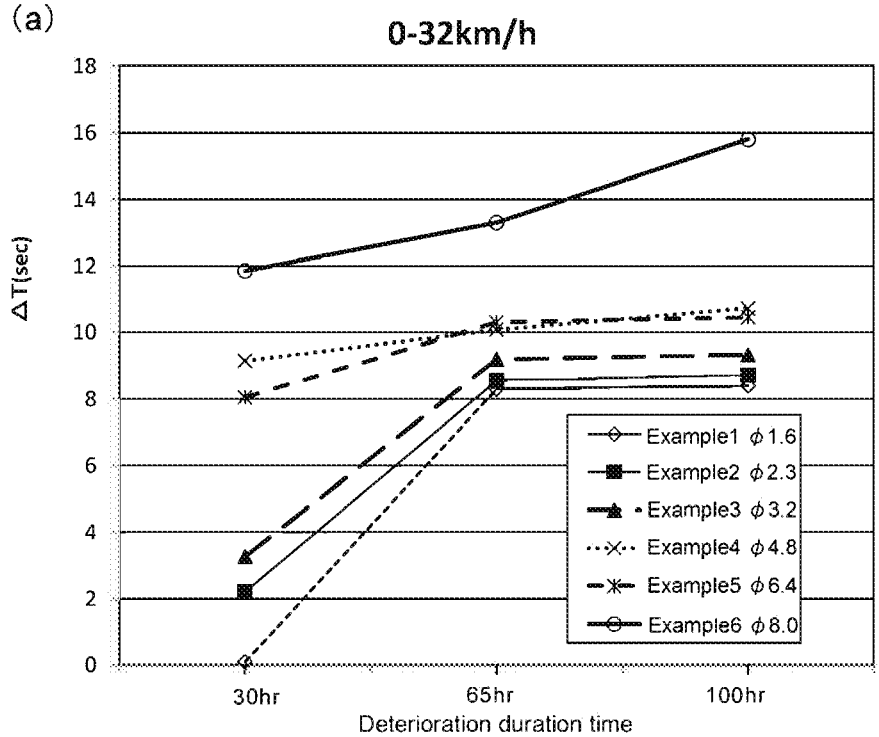
FIGS. 6(a) and 6(b) are charts illustrating differences $\Delta T$ between change points when the deteriorated catalysts were used in the Examples.
Figure 6:
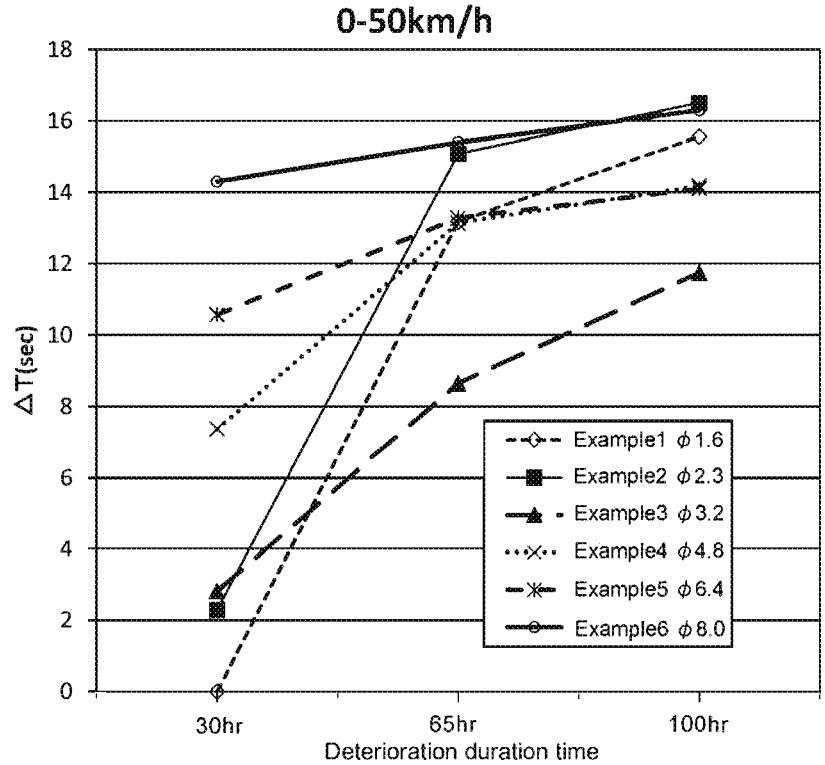

The catalyst deterioration detecting system of each Example was mounted on a saddle-type vehicle, and the saddle-type vehicle was driven at 60 km/h for 15 minutes, then decelerated to 0 km/h over 20 seconds, and then stopped in an idling state for 1 minute, and then either accelerated from 0 km/h to 32 km/h over 12 seconds or from 0 km/h to 50 km/h over 26 seconds. During this acceleration, the change point T1 where the temperature changes from temperature fall to temperature rise and the change point T2 where the temperature changes from temperature fall to temperature rise were derived, and the difference between the change points ($\Delta T = T2-T1$) was measured. FIG. 6 shows charts plotting the differences $\Delta T$ between change points with respect to the deterioration duration time of the respective deteriorated catalysts.

As is clear from the description of FIG. 6, in each of the Examples, $\Delta T$ increases with an increase in deterioration duration time. This shows that the system of the invention is capable of detecting $\Delta T$ corresponding to a progress in deterioration, and is useful in detecting catalyst deterioration. Further, the description of FIG. 6 shows that, compared to when the sheath diameter (time constant) of the downstream-side temperature detection means is the same as that of the upstream-side temperature detection means, when the absolute value of the time constant of the downstream-side temperature detection means is smaller (the sheath diameter is larger) than that of the upstream-side temperature detection means, the deterioration duration time is longer and easier to detect, and also, the degree of deterioration, as indicated by the emission amounts of CO, HC, and NOx, is easily reflected in $\Delta T$.

{Evaluation 1-2}

Figure 7:
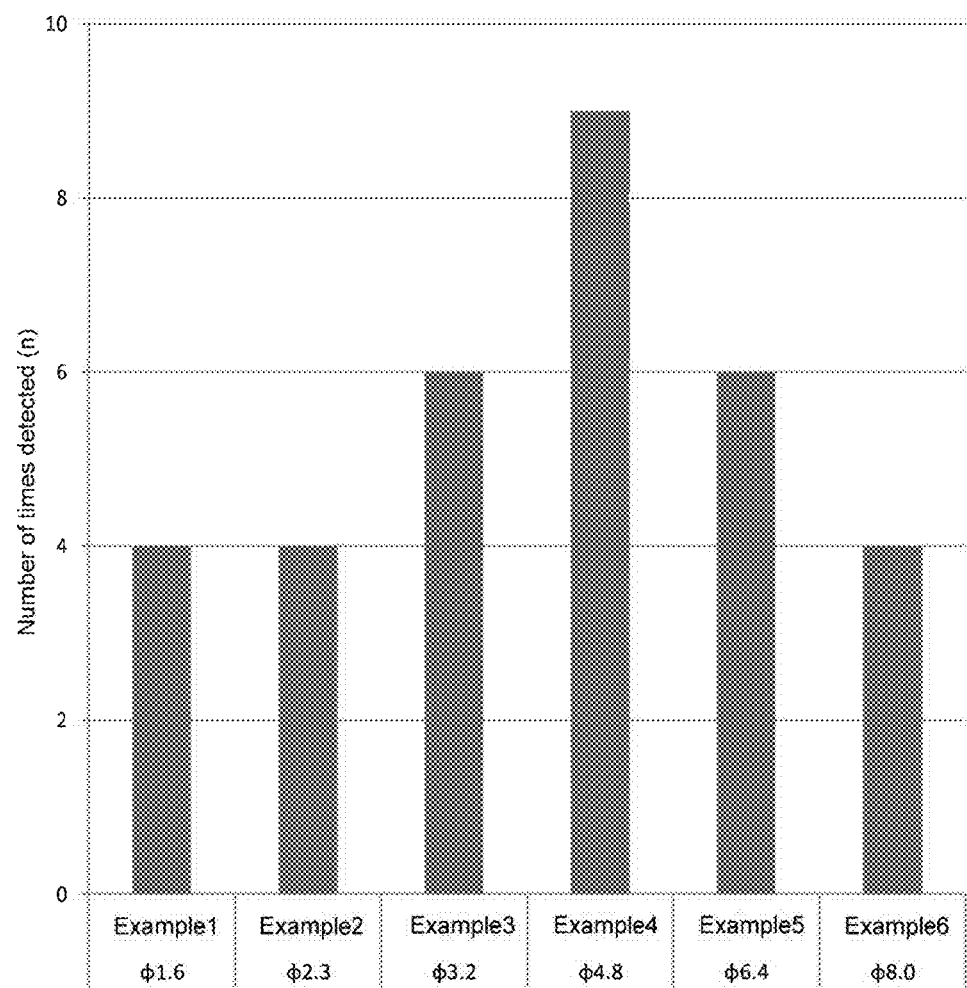
FIG. 7 is a chart illustrating the number of times catalyst deterioration was detected in the Examples.

Using each of the deteriorated catalysts for which the deterioration duration time was respectively 30, 65, or 100 hours, the same acceleration test as in Evaluation 1-1 was repeated twelve times (that is, acceleration from 0 km/h to 32 km/h was performed six times, and acceleration from 0 km/h to 50 km/h was performed six times). Of the twelve tests, the first acceleration test corresponding to initial warming-up (that is, the first acceleration from 0 km/h to 32 km/h and the first acceleration from 0 km/h to 50 km/h) is in the start-up stage and thus detection performance is less likely to be stable. So, the above first tests were excluded, and for a total of ten times of tests, the number of times that $\Delta T$ corresponding to the degree of catalyst deterioration was detected was counted. FIG. 7 shows the obtained chart. More specifically, determination as to whether $\Delta T$ corresponding to the degree of catalyst deterioration was verified or not was performed by: respectively recording, from upstream temperature data and downstream temperature data immediately after entering acceleration operation, the number of seconds after the change point at which the temperature changed to temperature rise (i.e., the cumulative time during the test); finding $\Delta T$ as the difference in time; and verifying whether the time difference $\Delta T$ became longer in accordance with deterioration duration time.

The description of FIG. 7 shows that, particularly when the sheath diameter is from 3.2 mm to 6.4 mm, the frequency of detecting $\Delta T$ corresponding to the degree of catalyst deterioration becomes highest.

It should be noted that, in Evaluation 1-2, when the number of times of detecting $\Delta T$ was counted by including the first acceleration test corresponding to initial warming-up (that is, the first acceleration from 0 km/h to 32 km/h and the first acceleration from 0 km/h to 50 km/h), Example 1 yielded six times, Example 2 yielded six times, Example 3 yielded six times, Example 4 yielded ten times, Example 5 yielded six times, and Example 6 yielded five times. This shows that the system of the present invention can sufficiently detect $\Delta T$ even when the first test, wherein detection performance is less likely to be stable, was included.

{Evaluation 1-3}

As illustrated in FIG. 6, in the aforementioned Evaluation 1-1, when the distance L2 between the outlet-side end portion 8b of the catalyst 8 and the temperature detection position of the downstream-side temperature detection means 6 was 60 mm, the result for Example 1 was $\Delta T=0$. However, when the same evaluation as in Evaluation 1-1 was performed for Example 1 by changing the distance L2 between the outlet-side end portion 8b of the catalyst 8 and the temperature detection position of the downstream-side temperature detection means 6 to 20 mm, $\Delta T$ with respect to deterioration duration time yielded the results shown in Table 2 below. Thus, in the catalyst deterioration detecting system of the invention, even in cases where the sheath diameter (time constant) of the downstream-side temperature detection means is the same as that of the upstream-side temperature detection means, catalyst deterioration can be detected sufficiently by adjusting L2.

TABLE 2

| ΔT of Example 1 (L2 = 20 mm) | | | |
|---|---|---|---|
| | 30 hr | 65 hr | (unit: seconds) 100 hr |
| 0 to 32 km/hr | 8.5 | 8.8 | 9.1 |
| 0 to 50 km/hr | 11.3 | 17.1 | 14.3 |

{Evaluation 2}

For the catalyst deterioration detecting system of the aforementioned Example 3, the detection of ΔT during deceleration testing was evaluated, opposite from the Evaluations 1-1 to 1-3. More specifically, using each of the deteriorated catalysts for which the deterioration duration time was respectively 30, 65, or 100 hours, deceleration tests were repeated five times each (that is, deceleration from 70 km/h to 50 km/h was performed five times). The first and second deceleration tests correspond to initial warming-up; so, for a total of three tests excluding the above two tests, evaluation was made as to whether or not ΔT corresponding to the degree of catalyst deterioration was verified. The result was that it was possible to detect ΔT all three times.

INDUSTRIAL APPLICABILITY

The present invention provides a highly versatile, inexpensive catalyst deterioration detecting system and catalyst deterioration detecting method capable of easily detecting deterioration of a catalyst without using an $O_2$ sensor.

REFERENCE SIGNS LIST

1: Pb sensor;
2: Ne sensor;
3: Th sensor;
4: $O_2$ sensor;
5: Upstream-side temperature detection means;
6: Downstream-side temperature detection means;
7: Monitor;
8: Catalyst;
8a: Inlet-side end portion;
8b: Outlet-side end portion;
9: Catalyst deterioration detecting system;
10: Engine control unit (ECU);
11: Engine;
12: Exhaust pipe;
50: Engine control system.

The invention claimed is:

1. A catalyst deterioration detecting system for detecting deterioration of a catalyst provided in an exhaust passage of an internal combustion engine, the system comprising:
   an upstream-side temperature detection means that detects a temperature of an exhaust on an upstream side of the catalyst;
   a downstream-side temperature detection means that detects a temperature of the exhaust on a downstream side of the catalyst; and either
   (A) a recognition unit that, during acceleration operation, recognizes a change point (T1) which is a time point at which the temperature detected by the upstream-side temperature detection means changes from temperature fall or constant temperature to temperature rise and a change point (T2) which is a time point at which the temperature detected by the downstream-side temperature detection means changes from temperature fall or constant temperature to temperature rise, and a determination unit that determines that the catalyst has deteriorated when a difference between the change points (ΔT=T2−T1) becomes equal to or longer than a predetermined time, or
   (B) a recognition unit that, during deceleration operation, recognizes a change point (T1') which is a time point at which the temperature detected by the upstream-side temperature detection means changes from temperature rise or constant temperature to temperature fall and a change point (T2') which is a time point at which the temperature detected by the downstream-side temperature detection means changes from temperature rise or constant temperature to temperature fall, and a determination unit that determines that the catalyst has deteriorated when a difference between the change points (ΔT'=T2'−T1') becomes equal to or longer than a predetermined time.

2. The catalyst deterioration detecting system according to claim 1, comprising:
   a recognition unit that, during acceleration operation, recognizes a change point (T1) which is a time point at which the temperature detected by the upstream-side temperature detection means changes from temperature fall to temperature rise, and a change point (T2) which is a time point at which the temperature detected by the downstream-side temperature detection means changes from temperature fall to temperature rise; and
   a determination unit that determines that the catalyst has deteriorated when a difference between the change points (ΔT=T2−T1) becomes equal to or longer than a predetermined time.

3. The catalyst deterioration detecting system according to claim 1, wherein the upstream-side temperature detection means and the downstream-side temperature detection means respectively have different time constants.

4. The catalyst deterioration detecting system according to claim 1, wherein:
   the upstream-side temperature detection means and the downstream-side temperature detection means are each constituted by a sheathed thermocouple; and
   a sheath diameter of the sheathed thermocouple used as the upstream-side temperature detection means is different from a sheath diameter of the sheathed thermocouple used as the downstream-side temperature detection means.

5. The catalyst deterioration detecting system according to claim 1, wherein a ratio (L2/L1) between a distance L1 from an inlet-side end portion of the catalyst to a temperature detection position of the upstream-side temperature detection means and a distance L2 from an outlet-side end portion of the catalyst to a temperature detection position of the downstream-side temperature detection means is from 0.18 to 5.00.

6. The catalyst deterioration detecting system according to claim 1, wherein the internal combustion engine is a gasoline engine.

7. A catalyst deterioration detecting method for detecting deterioration of a catalyst provided in an exhaust passage of an internal combustion engine, the method comprising:
   employing
      an upstream-side temperature detection means that detects a temperature of an exhaust on an upstream side of the catalyst, and
      a downstream-side temperature detection means that detects a temperature of the exhaust on a downstream side of the catalyst; and either (a) recognizing, during acceleration operation, a change point (T1) which is a time point at which the temperature detected by the upstream-side temperature detection means changes from temperature fall or constant temperature to temperature rise and a change point (T2) which is a time point at which the temperature detected by the downstream-side temperature detection means changes from temperature fall or constant temperature to temperature rise, and determining that the catalyst has deteriorated when a difference between the change points (ΔT=T2−T1) becomes equal to or longer than a predetermined time, or (b) recognizing, during deceleration operation, a change point (T1') which is a time point at which the temperature detected by the upstream-side temperature detection means changes from temperature rise or constant temperature to temperature fall and a change point (T2') which is a time point at which the temperature detected by the downstream-side temperature detection means changes from temperature rise or constant temperature to temperature fall, and determining that the catalyst has deteriorated when a difference between the change points (ΔT'=T2'−T1') becomes equal to or longer than a predetermined time.

* * * * *